United States Patent [19]

VanLare

[11] 4,283,488

[45] Aug. 11, 1981

[54] PHOTOGRAPHIC COMPOSITIONS AND ELEMENTS SPECTRALLY SENSITIZED WITH NEW METHINE DYES

[75] Inventor: Earl J. VanLare, Rochester, N.Y.

[73] Assignee: Eastman Kodak Company, Rochester, N.Y.

[21] Appl. No.: 180,261

[22] Filed: Aug. 22, 1980

[51] Int. Cl.[3] ............ G03C 1/02; G03C 1/18; G03C 1/19; G03C 1/22

[52] U.S. Cl. .................. 430/588; 430/570; 430/578; 430/579; 430/580; 430/581; 430/582; 430/583; 430/584; 430/585; 430/586; 430/587; 430/590; 430/592; 430/593; 430/594; 430/595

[58] Field of Search ............ 430/570, 578, 580, 581, 430/582, 583, 584, 585, 586, 587, 588, 590, 592, 594, 595, 579, 593

[56] References Cited

U.S. PATENT DOCUMENTS

| | | | |
|---|---|---|---|
| 3,397,220 | 8/1968 | Keebe | 260/448.2 |
| 3,734,739 | 5/1973 | Borror | 430/588 |
| 3,811,113 | 5/1974 | Rice | 260/140 |
| 3,816,494 | 9/1974 | Berger | 260/448.8 |
| 3,903,082 | 6/1974 | Berger | 260/243 R |
| 4,028,343 | 6/1977 | Amort et al. | 260/59 R |

*Primary Examiner*—Richard L. Schilling
*Attorney, Agent, or Firm*—Joshua G. Levitt

[57] ABSTRACT

Photo-sensitive silver halide compositions and elements are spectrally sensitized with new mathine dyes having a trialkylsilylalkyl group attached to a nitrogen atom in a heterocyclic nucleus of the dye.

9 Claims, No Drawings

PHOTOGRAPHIC COMPOSITIONS AND ELEMENTS SPECTRALLY SENSITIZED WITH NEW METHINE DYES

BACKGROUND OF THE INVENTION

1. Field of the Invention

The invention relates to new methine dyes, to novel intermediates useful in preparing such dyes, and to silver halide photographic compositions containing such dyes.

As used herein, the term "methine dye" means a dye comprising two nuclei, at least one of which is a heterocycle containing at least one nitrogen atom, the two nuclei being joined by a methine linkage, which is a conjugated chain of carbon atoms. Methine dyes include such dyes as cyanine, hemicyanine, and merocyanine dyes.

2. Description Relative to the Prior Art

Methine dyes are generally known, as is the use of such dyes as spectral sensitizers in silver halide photographic compositions. See, for example, Mees and James, *The Theory of the Photographic Process*, 3rd ed., N.Y., Macmillan, 1966, Chapter II, pp. 198-223, by L. S. G Brooker, *Sensitizing and Desensitizing Dyes*, 65-27328.

There is a constant search in the photographic art for new methine dyes to complement those already in use as spectral sensitizers. The present invention provides a new class of methine dyes. They have been found, unexpectedly, to be useful as spectral sensitizers for silver halide photographic compositions and thus provide the photographic chemist with a wider and more flexible choice of spectral sensitizers for any composition or process in which spectral sensitizing dyes are advantageously employed.

SUMMARY OF THE INVENTION

The invention provides methine dyes comprising first and second nuclei joined by a methine linkage, at least said first nucleus comprising a heterocyclic nitrogen ring or ring system having a trialkylsilylalkyl group attached to a nitrogen atom thereof.

It has been generally found that methine dyes having bulky, complex nuclei or bulky substituent groups attached to their nuclei are poor spectral sensitizers for silver halide photographic compositions, because they are sterically hindered from forming sufficiently compact aggregations adsorbed to the surface of silver halide grains. It has been unexpectedly found, however, that although the methine dyes of the present invention contain relatively bulky trialkylsilylalkyl substituent groups, they are very useful as spectral sensitizers for silver halide photographic compositions.

The invention also provides intermediates useful for preparing the methine dyes of the invention.

DESCRIPTION OF THE PREFERRED EMBODIMENTS

Methine dyes of the present invention are similar in structure to known methine dyes, except that they have a trialkylsilylalkyl group attached to a nitrogen atom in a heterocyclic ring or ring system of one or both of the nuclei of the dye. Preferred methine dyes are represented by the structural formula

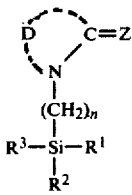

wherein:

D represents the atoms necessary to complete a substituted or unsubstituted heterocyclic ring or fused heterocyclic ring system, which constitutes the first nucleus of the methine dye;

Z represents the atoms necessary to complete a methine dye, including a methine linkage, a second nucleus and, if necessary, an associated ion to maintain charge neutrality;

$R^1$, $R^2$, and $R^3$ are the same or different alkyl groups having from 1 to 3 carbon atoms; and n is an integer from 1 to 6.

The first nucleus described above is derived from any of the basic heterocyclic nuclei conventionally employed in cyanine dyes. Some nuclei are well known to those skilled in the art. Some representative examples include: those of the thiazole series (e.g., thiazole, 4-methylthiazole, 5-methylthiazole, 4-phenylthiazole, 5-phenylthiazole, 4,5-dimethylthiazole, 4,5-diphenylthiazole, and 4-(2-thienyl)thiazole); those of the benzothiazole series (e.g., benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 4-phenylbenzothiazole, 5-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, tetrahydrobenzothiazole, 5,6-dimethoxybenzothiazole, 5,6-methylenedioxybenzothiazole, and 5-hydroxybenzothiazole); those of the naphthothiazole series (e.g., naphtho[1,2-d]thiazole, 5-methoxynaphtho[1,2-d]thiazole, 5-ethoxynaphtho[1,2-d]thiazole, 7-methoxynaphtho[2,1-d]-thiazole, and 8-methoxynaphtho[1,2-d]thiazole); those of the thieno[2,3-e]benzothiazole series (e.g., 4'methoxythieno[2,3-e]benzothiazole); those of the oxazole series (e.g., 4-methyloxazole, 5-methyloxazole, 4-phenyloxazole, 4,5-diphenyloxazole, 4-ethyloxazole, 4,5-dimethyloxazole, and 5-phenyloxazole); those of the benzoxazole series (e.g., benzoxazole, 5-chlorobenzoxazole, 5-phenylbenzoxazole, 5-methylbenzoxazole, 6-methylbenzoxazole, 5,6-dimethylbenzoxazole, 4,6-dimethylbenzoxazole, 5-methoxybenzoxazole, 6-methoxybenzoxazole, 5-ethoxybenzoxazole, 6-chlorobenzoxazole, 5-hydroxybenzoxazole, and 6-hydroxybenzoxazole); those of the naphthoxazole series (e.g., naphth[2,1-d]oxazole and naphth[1,2-d]oxazole); those of the selenazole series (e.g., 4-methylselenazole and 4-phenylselenazole); those of the benzoselenazole series (e.g., benzoselenazole, 5-chlorobenzoselenazole, 5-methoxybenzoselenazole, 5-hydroxybenzoselenazole, and tetrahydrobenzoselenazole); those of the naphthoselenazole series (e.g., naphtho[2,1-d]selenazole and naphtho[1,2-d]selenazole); those of the thiazoline series (e.g., thiazoline, and 4-methylthiazoline); those of the quinoline series (e.g., 2-quinoline, 4-quinoline, 6- methoxyquinoline, 7-methylquinoline, and 8-methylquinoline); those of the 1-isoquinoline series (e.g., isoquinoline and 3,4-dihydroisoquinoline); those of the 3,3-dialkyl-3H-indole series (e.g., 3,3-dimethyl-3H-indole, 3,3,5-trimethyl-3H-indole, and 3,3,7-trimethyl-3H-indole); those of the pyridine series (e.g., 2-pyridine, 4-pyridine, 3-methylpyridine, 4-methylpyridine, 5-methylpyridine, 6-methylpyridine, 3,4-dimethylpyridine, 3,5-dimethylpyridine, 3,6-dimethylpyridine, 4,5-dimethylpyridine, 4,6-dimethylpyridine, 4-chloropyridine, 5-chloropyridine, 6-chloropyridine, 3-hydroxypyridine, 4-hydroxypyridine, 5-hydroxypyridine, 6-hydroxypyridine, 3-phenylpyridine, 4-phenylpyridine, and 6-phenylpyridine); those of the imidazole series (e.g., imidazole, 4-methylimidazole, 5-ethylimidazole, 4-chloroimidazole, 4,5-dichloroimidazole, 4-methoxyimidazole, and 5-phenylimidazole); those of the benzimidazole series (e.g., benzimidazole, 4-methylbenzimidazole, 5-methylbenzimidazole, 6-methylbenzimidazole, 5,6-dichlorobenzimidazole, 5-chlorobenzimidazole, 5-phenylbenzimidazole, and 6-phenyl-benzimidazole); and those of the naphthimidazole series (e.g., naphth[2,1-d]imidazole and naphth[1,2-d]imidazole).

The second nucleus described above is of the same type as the first nucleus, or is of the type employed in merocyanine or hemicyanine dyes; (e.g., the nucleus that carries a negative charge in the zwitterionic resonance form of a merocyanine dye). Representative examples of acidic heterocyclic nuclei of the type employed in merocyanine dyes include: those of the 2-pyrazolin-5-one series (e.g., 3-methyl-1-phenyl-2-pyrazolin-5-one, 3-ethyl-1-phenyl-2-pyrazolin-5-one, and 1-methyl-3-phenyl-2-pyrazolin-5-one); those of the 3,4,6-triketohexahydropyrimidine or 2,6-diketo-4-thiohexahydropyrimidine series (e.g., barbituric acid or 2-thiobarbituric acid) as well as their 1-alkyl (e.g., 1-methyl, 1-ethyl, 1-n-propyl, and 1-n-heptyl), or 1,3-dialkyl (e.g., 1,3-dimethyl, 1,3-diethyl, and 1,3-di-n-propyl), cycloalkyl (such as dicyclohexyl), or 1,3-diaryl (e.g., 1,3-diphenyl and 1,3-di(p-chlorophenyl)), or 1-aryl (e.g. 1-phenyl, 1-p-chlorophenyl, and 1-p-ethoxycarbonylphenyl), or 1-alkyl-3-aryl (e.g., 1-ethyl-3-phenyl and 1-n-heptyl-3-phenyl) derivatives; those of the rhodanine series (e.g., rhodanine, 3-ethylrhodanine, 3-propylrhodanine, 3-butylrhodanine, 3-(p-carboxyphenyl)-rhodanine, and 3-(p-sulfophenyl)rhodanine); those of the hydantoin series (e.g. hydantoin, 1-(p-carboxyphenyl)-3-phenyl-hydantoin, and 1-ethyl-3-phenyl-hydantoin); those of the thiohydantoin series (e.g., 2-thiohydantoin, 1-p-carboxyphenyl-3-phenyl-3-thiohydantoin, 1-p-sulfophenyl-3-phenyl-2-thiohydantoin, and 1-ethyl-3-phenyl-2-thiohydantoin); and those of the 2-thio-2,4-oxazolidinedione series (e.g., 2-thio-2,4-oxazolindinedione, 3-(p-sulfophenyl)-2-thio-2,4-oxazolidinedione, and 3-ethyl-2-thio-2,4-oxazolidinedione). Another example is

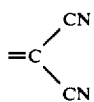

Structures for the second nucleus of a hemicyanine dye are also well known in the art. An example is

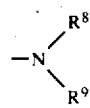

wherein $R^8$ and $R^9$ are the same or different hydrogen, alkyl, or aryl, including substituted forms thereof, or together complete a cyclic amino group.

The methine linkage described above joins together the first and second nuclei of the inventive methine dyes, comprises a chain of carbon atoms with alternating double and single bonds, and forms a part of the conjugated carbon atom chain which joins the terminal hetero atoms of the dye chromophore.

As is recognized by those skilled in the art, the length of the methine chain affects the spectral absorption of the dye. The longer the methine chain, the longer the wavelength of radiation absorbed by the dye, other things being equal. The number of carbon atoms in the methine chain can vary from one to seven or greater. Shorter chain lengths, which give dyes that absorb in the visible region of the spectrum, are preferred for most uses. The number of atoms in the methine chain is such that the conjugated carbon atom chain has an even number of alternating single and double bonds. Most conventional cyanine dyes have a methine chain containing an odd number of carbon atoms; for example one, three or five carbon atoms. Most conventional merocyanine dyes have a methine chain containing an even number of carbon atoms; for example two, or four carbon atoms.

Some especially preferred methine dyes of the present invention can be represented by the structural formula

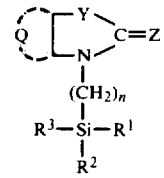

wherein:

Z, $R^1$, $R^2$, $R^3$, and n are as previously defined;

q represents the atoms necessary to complete a substituted or unsubstituted fused heterocyclic ring system which constitutes the first nucleus of the methine dye; and Y represents S, Se, O, or

wherein R represents substituted or unsubstituted alkyl having from 1 to 5 carbon atoms or substituted or unsubstituted aryl.

Some specific examples of especially preferred dyes of the invention are:

(1) 5,5′,6,6′-tetrachloro-1,1-diethyl-3,3′-bis(3-trimethylsilylpropyl)benzimidazolocarbocyanine iodide;

(2) 5,6-dichloro-1,3′-diethyl-3-(3-trimethylsilylpropyl) benzimidazolooxacarbocyanine iodide;

(3) 5,6-dichloro-1,3′-diethyl-3-(3-trimethylsilylpropyl) benzimidazolothiacarbocyanine iodide;

(4) 5,6-dichloro-1,3'-diethyl-3-(3-trimethylsilylpropyl)-4',5'-benzobenzimidazolothiacarbocyanine iodide;

(5) 5-{[5,6-dichloro-1-ethyl-3-(3-trimethylsilylpropyl)-2-benzimidazolinylidene]ethylidene}-3-ethylrhodanine;

(6) 5-{[5,6-dichloro-1-ethyl-3-(3-trimethylsilylpropyl)-2-benzimidazolinylidene]ethylidene}-3-ethyl-2-thio-2,4-oxazolidinedione;

(7) 3,3'-bis(3-trimethylsilylpropyl)thiacarbocyanine iodide;

(8) 9-methyl-3,3'-bis(3-trimethylsilylpropyl)thiacarbocyanine iodide;

(9) 9-ethyl-3,3'-bis(3-trimethylsilylpropyl)thiacarbocyanine iodide;

(10) 3,3'-bis(3-trimethylsilylpropyl)thiadicarbocyanine iodide;

(11) 1'-ethyl-3-(3-trimethylsilylpropyl)thia-2'-cyanine iodide;

(12) 3-ethyl-3'-(3-trimethylsilylpropyl)oxathiacarbocyanine iodide;

(13) 3-ethyl-3'-(3-trimethylsilylpropyl)-4,5-benzothiacarbocyanine iodide;

(14) 5-{[3-(3-trimethylsilylpropyl)-2-benzothiazolinylidene]ethylidene}-3-ethylrhodanine;

(15) 2-(3,3-dicyanoallylidene)-3-(3-trimethylsilylpropyl) benzothiazoline;

(16) 3,3'-bis(3-trimethylsilylpropyl)selenacarbocyanine iodide;

(17) 3,3'-bis(3-trimethylsilylpropyl)selenadicarbocyanine iodide;

(18) 1'-ethyl-3-(3-trimethylsilylpropyl)selena-2'-cyanine iodide;

(19) 3-ethyl-3'-(3-trimethylsilylpropyl)oxaselenocarbocyanine iodide; and

(20) 5,6-dichloro-1,3-diethyl-3'-(3-trimethylsilylpropyl) benzimidazoloselenacarbocyanine iodide.

Structural formulas for these specific dyes are set forth in Examples 1–23 below.

In order to prepare a methine dye of the present invention, a novel intermediate of the invention is first prepared. This is accomplished by reacting a methyl base that is useful to form a cyanine dye nucleus (as described previously) with a molar equivalent of a haloalkyltrialkylsilane. Where the haloalkyltrialkylsilane is a compound such as 3-chloropropyltrimethylsilane, it is desirable to add a molar equivalent of iodide (e.g. in the form of sodium iodide) to the reaction mixture in order to replace chloride with iodide in the silane before its reaction with a heterocyclic nitrogen atom in the methyl base. The reaction mixture is suspended in a non-aqueous non-reactive solvent such as acetonitrile and refluxed, the reflux time varying for different starting materials. The mixture is filtered while still hot to remove sodium halide, and ether is added to the filtrate to precipitate the solid intermediate. Additional yields can in some cases be obtained by concentrating the remaining filtrate and adding more ether. The novel intermediate thus formed is a heterocyclic nitrogen quaternary salt with a trialkylsilylalkyl group attached to the nitrogen. The intermediate is used to form the first, and in some embodiments also the second, nucleus of a methine dye of the invention.

Some examples of novel intermediates of the invention formed as described above are: 5,6-dichloro-1-ethyl-2-methyl-3-(3-trimethylsilylpropyl)benzimidazolium iodide; 2-methyl-3-(3-trimethylsilylpropyl)benzothiazolium iodide, and 2-methyl-3-(3-trimethylsilylpropyl)benzoselenazolium iodide.

In order to form a methine dye of the invention one of the novel intermediates of the invention is attached through a methine linkage to another compound useful to form a second cyanine, hemicyanine or merocyanine dye nucleus. Such compounds include all of the novel intermediates of the invention, all of the compounds useful to form cyanine dye nuclei as described above, all of the compounds useful to form the second nucleus of a merocyanine dye as descried above, and all of the compounds useful to form the second nucleus of a hemicyanine dye as described above.

Methods of joining two heterocyclic nuclei through a methine linkage are well known in the art and are described, for example, in Mees and James, *The Theory of the Photographic Process*, 3rd ed., N.Y., Macmillan, 1966, Chapter II, pp. 206–7 and 216, by L.G.S. Brooker, *Sensitizing and Densitizing Dyes*, 65–27328; in F.M. Hamer, *The Chemistry of Heterocyclic Compounds*, Vol. 18, "The Cyanine Dyes and Related Compounds", Interscience, N.Y., 1964; and in Ficken, *The Chemistry of Synthetic Dyes*, Vol. 4, Academic Press, N.Y., 1971. These methods are followed using the intermediate compounds described above to form the methine dyes of the invention.

The dyes of this invention spectrally sensitize photographic silver halide emulsions by extending the region of the spectrum to which the emulsion exhibits a photographic response. The photographic silver halide emulsions include negative working, reversal, and direct positive emulsions comprised of, for example, silver chloride, silver bromide, silver bromoiodide, silver chlorobromide, silver chloroiodide, silver chlorobromoiodide crystals or mixtures of such crystals. The emulsions are coarse or fine grain emulsions and are prepared by a variety of techniques, e.g., single jet emulsions such as those described in Trivelli and Smith, *The Photographic Journal*, Vol. LXXIX, May 1939 (pp. 330–338), double jet emulsions such as Lippmann emulsions, ammoniacal emulsions, thiocyanate or thioether ripened emulsions such as those described in Nietz et al U.S. Pat. No. 2,222,264 issued Nov. 19, 1940; Illingsworth U.S. Pat. No. 3,320,069 issued May 17, 1967 and McBride U.S. Pat. No. 3,271,157 issued Sept. 6, 1966. The silver halide emulsions form latent images predominantly on the surface of the silver halide grains, or predominantly on the interior of the silver halide grains such as those described in Davey et al U.S. Pat. No. 2,592,250 issued May 8, 1952; Porter et al U.S. Pat. No. 3,206,313 issued Sept. 14, 1565; Berriman U.S. Pat. No. 3,367,778 issued Feb. 6, 1968 and Bacon et al U.S. Pat. No. 3,447,927 issued June 3, 1969. If desired, mixtures of such surface and internal image-forming emulsions are made, such as described in Luckey et al U.S. Pat. No. 2,996,382 issued Aug. 15, 1961. In some embodiments, the silver halide emulsions are regular grain emulsions such as the type described in Klein and Moisar, J. Phot. Sci., Vol. 12, No. 5, Sept./Oct., 1964, pp. 242–251. Negative type emulsions as well as direct positive emulsions are useful and are made as described in Leermakers U.S. Pat. No. 2,184,013 issued Dec. 19, 1939; Kendall et al U.S. Pat. No. 2,541,472 issued Feb. 13, 1951; Schouwenaars British Pat. No. 723,019 issued Feb. 2, 1955; Illingsworth et al French Pat. No. 1,520,821 issued Mar. 4, 1968; Illingsworth U.S. Pat. No. 3,501,307 issued Mar. 17, 1970; Ives U.S. Pat. No. 2,563,785 issued Aug. 7, 1951; Knott et al U.S. Pat. No. 2,456,953 issued Dec. 21, 1948 and Land U.S. Pat. No. 2,861,885 issued Nov. 25, 1958.

The silver halide emulsions are unwashed or washed to remove soluble salts after precipitation of the silver halide. In the latter case, the soluble salts are removed by chill-setting and leaching or the emulsion is coagulation washed, e.g., by the procedures described in Hewitson et al U.S. Pat. No. 2,618,556 issued Nov. 18, 1952; Yutzy et al U.S. Pat. No. 2,614,928 issued Oct. 21, 1952; Yackel U.S. Pat. No. 2,565,418 issued Aug. 21, 1951; Hart et al U.S. Pat. No. 3,241,969 issued Mar. 22, 1966 and Waller et al U.S. Pat. No. 2,489,341 issued Nov. 29, 1949.

The dyes of this invention are advantageously incorporated in the washed, finished emulsion. The dyes are added from solutions in appropriate solvents which are compatible with the emulsion and which are substantially free from deleterious effects on the light-sensitive materials.

The types of silver halide emulsions to be sensitized with the new dyes of this invention include those prepared with hydrophilic colloids that are known to be satisfactory vehicles for dispersed silver halides, for example, emulsions comprising both naturally-occurring substances such as proteins, for example, gelatin, gelatin derivatives, cellulose derivatives, polysaccharides such as dextran, and gum arabic; and synthetic polymeric substances (e.g., water-soluble polyvinyl compounds such as poly(vinylpyrrolidone) and acrylamide polymers). In some embodiments the photographic emulsions also contain, alone or in combination with hydrophilic, water-permeable colloids, other synthetic polymeric vehicle compounds such as dispersed vinyl compounds such as in latex form and particularly those which increase the dimensional stability of the photographic materials. Representative synthetic polymers include those described in Nottort U.S. Pat. No. 3,142,568 issued July 28, 1964; White U.S. Pat. No. 3,193,386 issued July 6, 1965; Houck et al U.S. Pat. No. 3,062,674 issued Nov. 6, 1962; Houck et al U.S. Pat. No. 3,220,844 issued Nov. 30, 1965; Ream et al U.S. Pat. No. 3,287,289 issued Nov. 22, 1966; and Dykstra U.S. Pat. No. 3,411,911 issued Nov. 19, 1968. Other materials include water-insoluble polymers of alkyl acrylates and methacrylates, acrylic acid, sulfoalkyl acrylates or methacrylates, those which have cross-linking sites which facilitate hardening or curing as described in Smith U.S. Pat. No. 3,488,708 issued Jan. 6, 1970, and those having recurring sulfobetaine units as described in Dykstra Canadian Pat. No. 774,054.

The concentration of the new dyes in the emulsion embodiments vary, e.g., from about 25 to 1000 mg. per mole of silver in flowable emulsion. The specific concentration will vary according to the type of light-sensitive material in the emulsion and the effects desired. The suitable and most economical concentration for a given emulsion will be apparent to those skilled in the art upon making the tests and observations customarily used in the art of emulsion making.

To prepare a gelatin-silver halide emulsion sensitized with one of the dyes of this invention, the following procedure is satisfactory. A quantity of the dye is dissolved in a suitable solvent and a volume of this solution containing from 25 to 1000 mg. of dye per mole of silver is slowly added to the gelatin-silver halide emulsion. With most of the dyes, 50 to 500 mg. of dye per mole of silver suffices to produce the maximum sensitizing effect with the ordinary gelatin-silver bromide (including bromoiodide and chlorobromide) emulsions. With fine grain emulsions, which include most of the ordinarily employed gelatin-silver chloride emulsions, somewhat larger concentrations of dye are sometimes necessary to obtain the optimum sensitizing effect. While this procedure has dealt with emulsions comprising gelatin, it will be appreciated that these remarks apply also to an emulsion wherein all or part of the gelatin is substituted by another suitable hydrophilic colloid as mentioned above. Binderless light-sensitive silver halide grains are also spectrally sensitized with the dyes of this invention.

Some embodiments of photographic silver halide emulsions spectrally sensitized in accordance with this invention also contain chemical sensitizers, stabilizers, antifoggants, development modifiers, hardeners, vehicles, plasticizers, coating aids, or other spectral sensitizing dyes, and in some cases are coated on supports, such as those described and referred to in *Product Licensing Index*, Vol. 92, December, 1971, publication 9232, pages 107–110. Such emulsions are useful in photographic elements which may contain developing agents, antistatic layers, matting agents, brighteners, absorbing and filter dyes, and color-forming couplers, as described and referred to in the above-mentioned *Product Licensing Index*, pages 108–110. Suitable methods for processing of photographic silver halide grains spectrally sensitized in accordance with this invention are described and referred to on page 110 of the above-identified *Product Licensing Index*.

Photographic elements incorporating the sensitized silver halide emulsions of this invention are made by coating the emulsions on a suitable support, of which a wide variety are known in the art. Examples of suitable supports are cellulose nitrate film, cellulose acetate film, poly(vinyl acetal) film, poly(ethylene terephthalate) film, polycarbonate film and related films or resinous materials, as well as glass, paper, and metal. Conventionally, a flexible support is employed, such as a paper support, which can be partially acetylated or coated with baryta and/or an alpha-olefin polymer, particularly a polymer of an alpha-olefin containing 2 to 10 carbon atoms such as polyethylene, polypropylene, an ethylenebutene copolymers. Suitable procedures for preparing photographic elements incorporating this invention are described and referred to on page 109 of the above-identified *Product Licensing Index*, vol. 92, December 1971.

The following examples are included to further illustrate the preparation and use of preferred embodiments of the invention. Examples 1–3 relate to the preparation of novel intermediates of the invention.

EXAMPLE 1

Preparation of
5,6-dichloro-1-ethyl-2-methyl-3-(3-trimethylsilyl-propyl)benzimidazolium iodide $C_{16}H_{25}Cl_2IN_2Si$    MW = 471.3

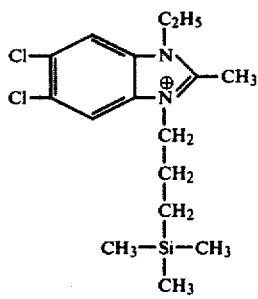

5,6-Dichloro-1-ethyl-2-methylbenzimidazole (22.9 g, 0.10 moles), 3-chloropropyltrimethylsilane (15.0 g, 0.10 moles), and sodium iodide (15.0 g, 0.10 moles) were suspended in acetonitrile (200 ml) and with stirring the mixture was refluxed for 17 hours. It was filtered while hot to remove NaCl and the filtrate treated with ether (300 ml). Solid which precipitated was filtered off, washed with ether and dried. Yield 11.3 g (24%) mp 213°–5°. Additional crops were obtained by concentrating the filtrates and adding more ether. The mp of each crop was lower and less exact than the previous crop but all crops contained at least some product.

EXAMPLE 2

Preparation of
2-Methyl-3-(3-trimethylsilylpropyl)benzothiazolium iodide $C_{14}H_{22}INSSi$    MW = 391.4

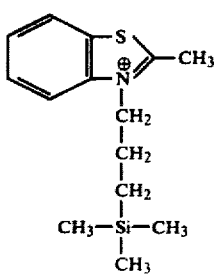

2-Methylbenzothiazole (14.9 g, 0.10 moles), 3-chloropropyltrimethylsilane (15.0 g, 0.10 moles) and sodium iodide (15.0 g, 0.10 moles) were all suspended in acetonitrile (250 ml) and with stirring the mixture was heated at reflux for four days. The mixture was filtered while hot to remove sodium chloride, the solid was washed with acetonitrile and the filtrate was concentrated to dryness. The residue was stirred with ether and dried. Yield 9 16 g (25%) mp 203°–205°.

EXAMPLE 3

Preparation of
2-methyl-3-(3-trimethylsilylpropyl)benzoselenazolium iodide $C_{14}H_{22}INSeSi$    MW = 438.3

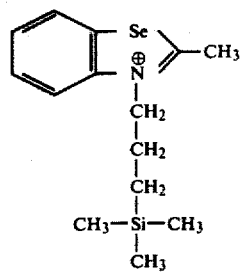

This compound was prepared in a manner similar to that of Example 2 using the same molar quantities of reactants except that 2-methylbenzoselenazole was used in place of 2-methylbenzothiazole. Yield 6.3 g (14%) mp 220°–221°.

Examples 4–23 illustrate the preparation of preferred dyes of the invention. Examples 4–9 relate to dyes prepared from the intermediate of Example 1. Examples 10–18 relate to dyes prepared from the intermediate of Example 2. Examples 19–23 relate to dyes prepared from the intermediate of Example 3.

EXAMPLE 4

5,5',6,6'-Tetrachloro-1,1'-diethyl-3,3'-bis(3-trimethyl-silylpropyl)benzimidazolocarbocyanine iodide $C_{33}H_{47}Cl_4IN_4Si$    MW = 824.6

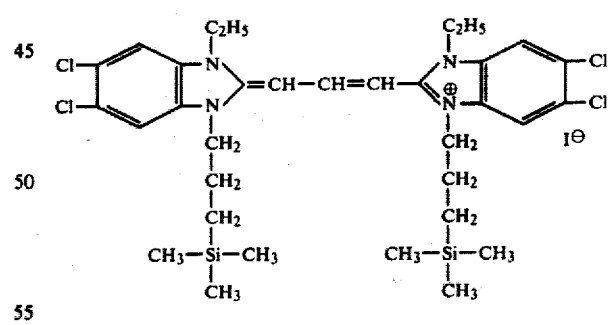

Sodium (0.58 g, 0.025 moles) was added to ethyl alcohol (50 ml). When the reaction was complete the intermediate (Ex. 1) (4.7 g, 0.01 moles) and chloral alcoholate (1.0 g, 0.005 moles) were added in order with stirring and the mixture was refluxed 45 minutes, filtered while hot to remove sodium chloride and the filtrate chilled. The solid dye which separated was filtered off, washed with water and dried. Yield 0.75 g (18%). The dye was purified by two recrystallizations from dimethyl formamide (30 ml)/methanol (60 ml). Yield 0.50 g (12%).

EXAMPLE 5

5,6-Dichloro-1,3'-diethyl-3-(3-trimethylsilylpropyl)benzimidazolooxacarbocyanine iodide C$_{27}$H$_{34}$Cl$_2$IN$_3$OSi    MW = 642.5

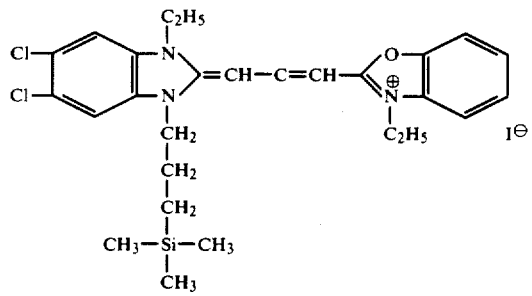

The intermediate (Ex. 1) (2.40 g, 0.005 moles) and 2-(2-acetanilidovinyl)-3-ethylbenzoxazolium iodide (2.2 g, 0.005 moles) were suspended in dimethylacetamide (10 ml). Triethylamine (0.7 ml) was added and the mixture allowed to stand for 5 min. It was then slowly heated to reflux. Dye precipitated from the hot reaction mixture. After 2 min. at reflux the reaction mixture was chilled, the solid dye was filtered off and dried. Yield 1.6 g (50%). The dye was purified by two recrystallizations from dimethylformamide (65 ml)/methanol (120 ml). Yield 1.25 g (39%).

EXAMPLE 6

5,6-Dichloro-1,3'-diethyl-3-(3-trimethylsilylpropyl)benzimidazolothiacarbocyanine iodide C$_{27}$H$_{34}$Cl$_2$IN$_3$SSi    MW = 658.5

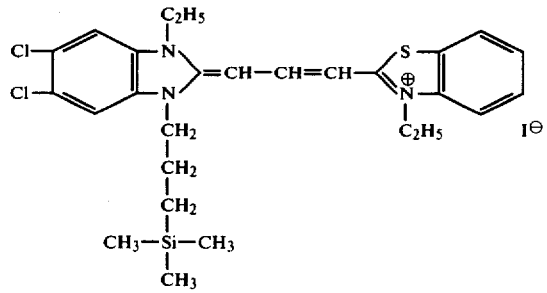

This dye was prepared in the same way as the dye of Example 5 using the same molar quantities of reactants except that 2-(2-acetanilidovinyl)-3-ethylbenzothiazolium iodide was used in place of 2-(2-acetanilidovinyl)-3-ethylbenzoxazolium iodide. Yield 2.1 g (63%). The dye was purified by two recrystallizations from dimethylformamide/methanol (75/150 ml for the first recrystallization and 45/200 ml for the second). Yield 1.25 g (38%).

EXAMPLE 7

5,6-Dichloro-1,3'-diethyl-3-(3-trimethylsilylpropyl-4',5'-benzobenzimidazolothiacarbocyanine iodide C$_{31}$H$_{36}$Cl$_2$IN$_3$SSi    MW = 708.5

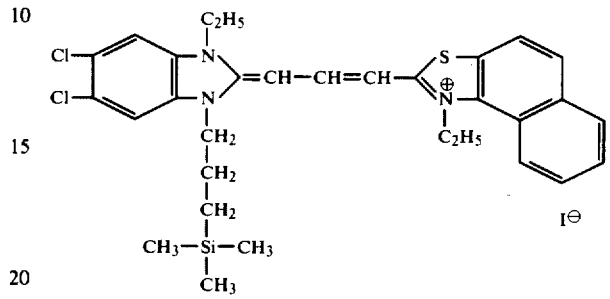

This dye was prepared in the same way as the dye of Example 5 using the same molar quantities of reactants except that 2-(2-anilinovinyl)-1-ethylnaphtho[1,2-d]thiazolium-p-toluenesulfonate was used in place of 2-(2-acetanilidovinyl)-3-ethylbenzoxazolium iodide and acetic anhydride (0.6 ml) was also added. Yield 3.4 g (97%). The dye was purified by two recrystallizations from dimethylformamide (90 ml)/methanol (75 ml). Yield 2.45 g (70%).

EXAMPLE 8

5-{[5,6-Dichloro-1-ethyl-3-(3-trimethylsilylpropyl)-2-benzimidazolinylidene]-ethylidene}-3-ethylrhodanine C$_{22}$H$_{29}$Cl$_2$N$_3$OS$_2$Si    MW = 514.6

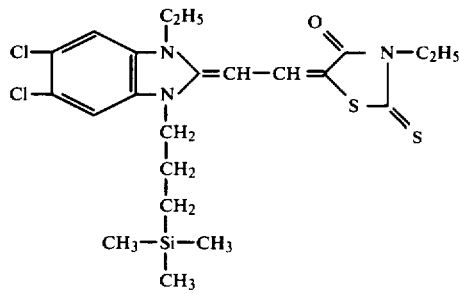

The intermediate (Example 1) (2.40 g, 0.005 moles) and 5-acetanilido-methylene-3-ethylrhodanine (1.6 g, 0.005 moles) were suspended in pyridine (10 ml) to which triethylamine (0.7 ml) was subsequently added. The reaction mixture was refluxed for 10 minutes, chilled, diluted with ethyl alcohol (30 ml), seeded to augment crystallization and chilled further. The solid dye was collected by filtration and dried. Yield 1.1 g (42%). The dye was purified by two recrystallizations from pyridine (15 ml)/methanol (50 ml). Yield 0.8 g (31%).

EXAMPLE 9

5-{[5,6-Dichloro-1-ethyl-3-(3-trimethylsilylpropyl)-2-benzimidazolinylidene]ethylidene}-3-ethyl-2-thio-2,4-oxazolidinedione $C_{22}H_{29}Cl_2N_3O_2SSi$  MW = 498.5

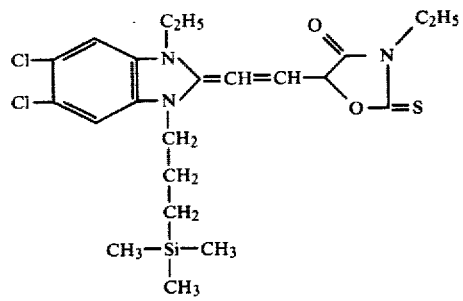

This dye was prepared in the same way as the dye of Example 8 using the same molar quantities of reactants except that 5-acetanilidovinyl-3-ethyl-2-thio-2,4-oxazolidinedione was used in place of 5-acetanilidovinyl-3-ethylrhodanine. Yield 1.1 g (44%). The dye was purified as in Example 8 using pyridine (10 ml)/methanol (50 ml). Yield 0.75 g (30%).

EXAMPLE 10

3,3'-Bis(3-trimethylsilylpropyl)thiacarbocyanine iodide $C_{29}H_{41}IN_2S_2Si_2$  MW = 664.8

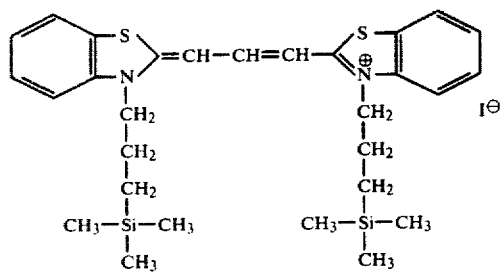

The intermediate (Example 2(3.0 g, 0.0075 moles) was suspended in pyridine (8 ml) to which triethylorthoformate (1.1 g, 0.0075 moles) was subsequently added. The mixture was refluxed 5 min. The dye separated while hot. After chilling, the mixture was filtered to remove the dye which was washed with ethyl alcohol and dried. Yield 1.4 g (55%). It was purified by two recrystallizations from methanol 55 ml/g. Yield 1.0 g (39%).

EXAMPLE 11

9-Methyl-3,3'-bis(3-trimethylsilylpropyl) thiacarbocyanine iodide $C_{30}H_{43}IN_2S_2Si_2$  MW = 678.8

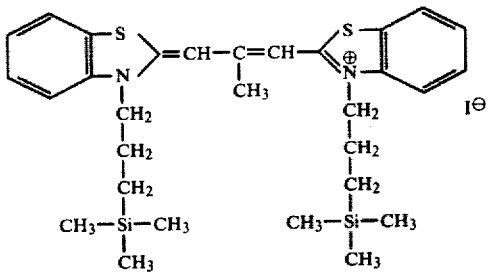

This dye was prepared in the same way as the dye of Example 10 using the same molar quantities of reactants except that triethylorthoacetate was used in place of triethylorthoformate. Yield 0.50 g (19%). The dye was purified by two recrystallizations from methanol (60 ml/g). Yield 0.35 g (13%).

EXAMPLE 12

9-Ethyl-3,3'-bis(3-trimethylsilylpropyl)thiacarbocyanine iodide $C_{31}H_{43}IN_2S_2Si_2$  MW = 692.8

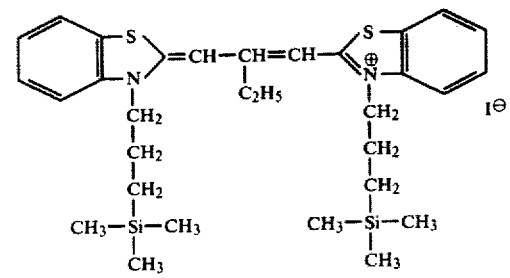

This dye was prepared in the same way as the dye of Example 10 using the same molar quantities of reactants except that triethylorthoproprionate was used in place of triethylorthoformate. Yield 1.1 g (40%). The dye was purified as in Example 10 (50 ml/g methanol). Yield (24%).

EXAMPLE 13

3,3'-Bis(3-trimethylsilylpropyl)thiadicarbocyanine iodide

C₃₁H₄₃IN₂S₂Si₂   MW = 690.8

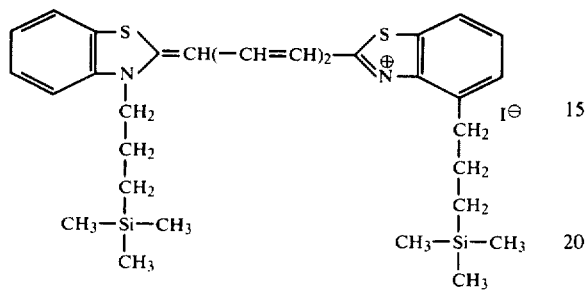

The dye was prepared in the same way as the dye of Example 10 using the same molar quantities of reactants except that 1,3,3-tri-methoxypropene was used in place of triethylorthoformate. Yield 0.80 g (29%). The crude dye was extracted with 3 90 ml portions of methanol and the extracts concentrated to dryness. The extracted dye was recrystallized from methanol 175 ml/g. Yield 0.4 (16%).

EXAMPLE 14

1'-Ethyl-3-(3-trimethylsilylpropyl)thia-2'-cyanine iodide

C₂₅H₃₁IN₂SSi   MW = 546.6

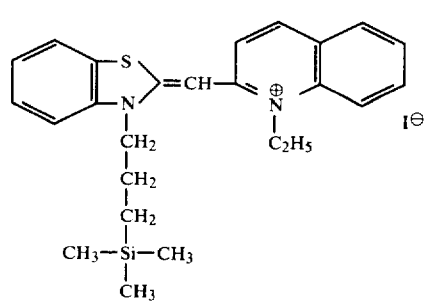

The intermediate (Example 2) (1.5 g, 0.0038 moles) and 1-ethyl-2-phenylthioquinolinium p-toluenesulfonate (1.7 g, 0.0039 moles) were suspended in ethyl alcohol (10 ml) to which triethylamine (1.1 g) was subsequently added. The mixture was refluxed 10 min, chilled and filtered to remove the solid dye which was washed with ethyl alcohol and dried. Yield 1.7 g (81%). The dye was purified by recrystallization from methanol. Yield 1.3 g (62%).

EXAMPLE 15

3-Ethyl-3'-(3-trimethylsilylpropyl)oxathiacarbocyanine iodide

C₂₅H₃₁IN₂OSSi   MW = 562.6

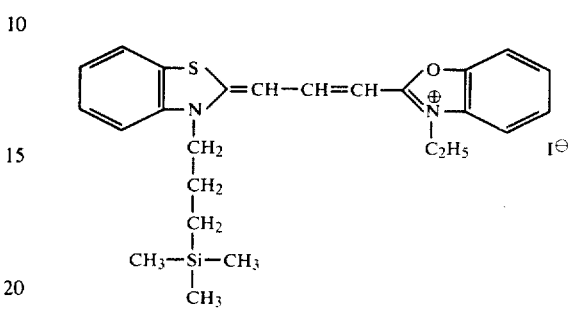

This dye was prepared in the same way as the dye of Example 14 using the same molar quantities of reactants except that 2-(2-acetanilidovinyl)-3-ethylbenzoxazolium iodide was used in place of 1-ethyl-2-phenylthioquinolinium p-toluenesulfonate. Yield 1.7 g (79%). The dye was purified by two recrystallizations from methanol (35 ml/g). Yield 0.80 g (38%).

EXAMPLE 16

3-Ethyl-3'-(3-trimethylsilylpropyl)-4,5-benzothiacarbocyanine iodide

C₂₉H₃₃IN₂S₂Si   MW = 628.7

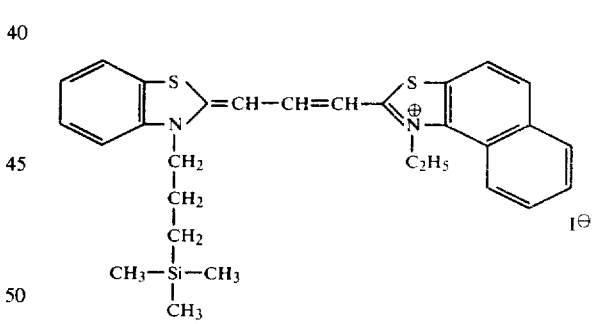

This dye was prepared in the same way as the dye of Example 14 using the same molar quantities of reactants except that 2-(2-anilinovinyl)-1-ethylnaphtho[1,2-d]thiazolium p-toluenesulfonate was used in place of 1-ethyl-2-phenylthioquinolinium p-toluenesulfonate and acetic anhydride (0.5 ml) was also added. The crude dye was extracted with methanol 150 ml. The extract was chilled and filtered to yield 0.45 g solid dye. The unextracted solid was recrystallized from 225 ml methanol to yield 0.50 g solid dye. The combined solid dye was dissolved in 475 ml hot methanol. The solution concentrated to 250 ml volume, chilled and filtered to remove the pure dye. Yield 0.70 g (30%).

EXAMPLE 17

5-{[3-(3-Trimethylsilylpropyl)-2-benzothiazolinylidene]ethylidene}-3-ethylrhodanine $C_{20}H_{26}N_2OS_3Si$ MW = 434.7

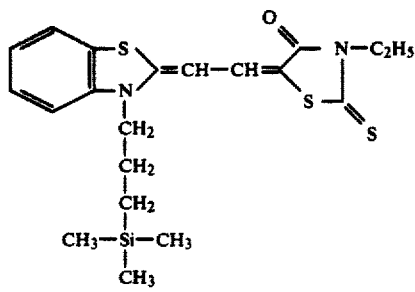

This dye was prepared in the same way as the dye of Example 14 using the same molar quantities of reactants except that 5-acetanilidomethylene-3-ethylrhodanine was used in place of 1-ethyl-2-phenylthioquinolinium p-toluenesulfonate. Yield 1.2 g (72%). The dye was purified by two recrystallizations from pyridine (40 ml)/methanol (60 ml). Yield 1.1 g (66%).

EXAMPLE 18

2(3,3-Dicyanoallylidene)-3-(3-trimethylsilylpropyl)benzothiazol $C_{18}H_{21}N_3SSi$ MW = 339.5

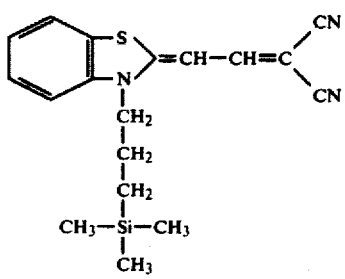

This dye was prepared in the same way as the dye of Example 14 using the same molar quantities of reactants except that anilinomethylenemalononitrile was used in place of 1-ethyl-2-phenylthioquinolinium p-toluenesulfonate and acetic anhydride (0.5 ml) was also added. Yield 0.90 g (69%). The dye was purified by two recrystallizations from pyridine (20 ml)/methanol (80 ml). Yield 0.85 g (66%).

EXAMPLE 19

3,3'-Bis(3-trimethylsilylpropyl)selenacarbocyanine iodide $C_{29}H_{41}IN_2Se_2Si_2$ MW = 758.6

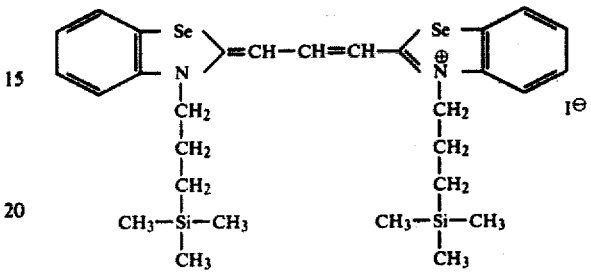

The intermediate (Example C) (2.2 g, 0.005 moles) was suspended in pyridine (10 ml). Diethoxymethyl acetate (1.6 g, 0.01 moles) was added and the mixture was refluxed for 20 min. Solid dye separated while hot. The mixture was chilled and the solid dye removed by filtration, washed with acetone and dried. Yield 1.2 g (63%). It was purified by two recrystallizations from methanol (170 ml/g). Yield 0.80 g (42%).

EXAMPLE 20

3,3'-Bis(3-trimethylsilylpropyl)selenadicarbocyanine iodide $C_{31}H_{43}IN_2Se_2Si_2$ MW = 784.6

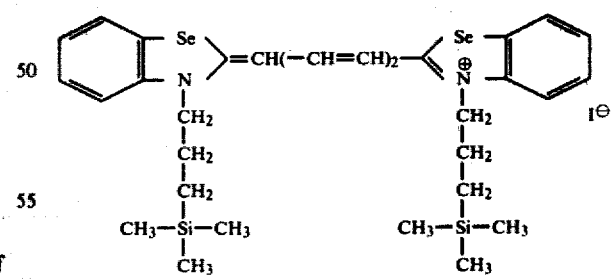

This dye was prepared in the same way as the dye of Example 19 using the same molar quantities of reactants except that 1,3,3-trimethoxypropene was used in place of diethoxymethyl acetate. Yield 0.5 g (26%). It was purified by two recrystallizations from methanol (500 ml/g). Yield 0.40 g (21%).

EXAMPLE 21

1'-Ethyl-3-(3-trimethylsilylpropyl)selena-2'-cyanine iodide

C25H31IN2SeSi      MW = 593.5

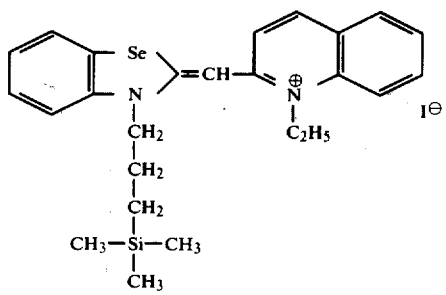

The intermediate (Example 3) (2.2 g, 0.005 moles) and 1-ethyl-2-phenylthioquinolinium p-toluenesulfonate (2.2 g, 0.005 moles) were suspended in ethyl alcohol and heated. Triethylamine (1.4 g) was subsequently added when the suspension reached refluxing temperature and refluxing was continued for ten minutes and then chilled. The solid dye was filtered off, washed with ethyl alcohol and dried. Yield 1.55 g (51%). It was purified by two recrystallizations from methanol. Yield 1.20 g (39%).

EXAMPLE 22

3-Ethyl-3'-(3-trimethylsilylpropyl)oxaselenocarbocyanine iodide

C25H31IN2OSeSi      MW = 609.5

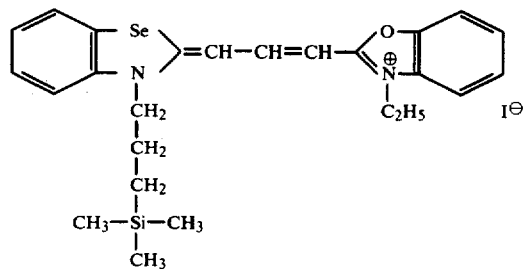

The intermediate (Example 3) (2.2 g, 0.005 moles) and 2-(2-acetanilidovinyl-3-ethyl-benzoxazolium iodide (2.2 g, 0.005 moles) were suspended in ethyl alcohol (10 ml) to which triethylamine (1.4 ml) was subsequently added. The mixture was refluxed 10 min., chilled and filtered to remove the solid dye. The dye was washed with ethyl alcohol and dried. Yield 1.2 g (40%). It was purified by two recrystallizations from methanol (25 ml/g). Yield 0.80 g (27%).

EXAMPLE 23

5,6-Dichloro-1,3-diethyl-3'-(3-trimethylsilylpropyl)benzimidazoloselenacarbocyanine iodide C27H34Cl2IN3SeSi      MW = 705.4

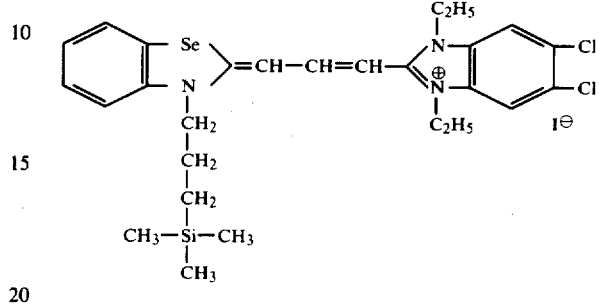

The intermediate (Example 3) 2.2 g, (0.005 moles) and 2-anilinovinyl-5,6-dichlor-1,3-diethylbenzimidazolium iodide (2.45 g, 0.005 moles) were suspended in dimethylacetamide (15 ml) to which acetic anhydride (0.7 ml) had been added. The suspension was heated with stirring before triethylamine (2.1 ml) was added. Heating and stirring was continued for 10 min. The mixture was chilled and filtered to remove the solid dye. The dye was washed with acetone and dried. Yield 1.6 g (46%). It was purified by two recrystallizations from methanol (125 ml/g). Yield 0.90 g (26%).

Relevant constants for the dyes of Examples 4–23 are given in Table 1.

TABLE 1

| Dye of Example # | MP °C. | Wavelength of Maximum Radiation Absorption In Methanol (nm) | Maximum Absorption Coefficient $\epsilon$ max $\times$ $10^{-4}$ |
| --- | --- | --- | --- |
| 4 | 266–267 | 516 | 19.0 |
| 5 | 295–296 | 485 | 10.8 |
| 6 | 283–284 | 520 | 9.4 |
| 7 | 258–259 | 541 | 10.3 |
| 8 | 210–212 | 521 | 14.6 |
| 9 | 216–217 | 499 | 14.4 |
| 10 | 280–281 | 559 | 16.6 |
| 11 | 275–276 | 545 | 13.0 |
| 12 | 230–231 | 549 | 11.7 |
| 13 | 241–242 | 652 | 23.8 |
| 14 | 261–262 | 484 | 5.1 |
| 15 | 247–248 | 519 | 15.3 |
| 16 | 261–262 | 576 | 14.3 |
| 17 | 255–257 | 524 | 8.8 |
| 18 | 207–209 | 449 | 8.3 |
| 19 | 283–284 | 571 | 12.8 |
| 20 | 223–224 | 664 | 23.6 |
| 21 | 267–268 | 490 | 4.5 |
| 22 | 242–243 | 526 | 14.6 |
| 23 | 291–292 | 519 | 8.7 |

EXAMPLE 24

Use of the inventive dyes as spectral sensitizers in silver halide compositions

The individual dyes were added to separate portions of a 0.2 μm sulfur and gold sensitized, mono-dispersed gelatino silver bromoiodide emulsion containing 2.5 mole % iodide at the concentrations indicated in Table 2 and the resulting mixtures were coated to obtain silver coverage of 1.07 g/m² on a cellulose ester support. A sample of each coating was exposed in a spectral sensitometer to a quartz-halogen light source through a Wratten 80B color correcting filter, diffraction grating with filters to remove second order transmission, and superimposed step wedge. The coatings were developed in a roller transport processor for 80 sec. at 23° C. in an N-methyl-p-aminophenol/hydroquinone developer, fixed, washed and dried. A Density vs. Log Exposure curve (D log E) was produced for each coating at 400 nm and at each 10 nm interval between 400 nm and 700 nm. The speed at 0.3 density units above fog was read from each D log E curve, adjusted for a uniform energy distribution over the spectral range, and plotted against wavelength to obtain a relative log spectral sensitivity curve. The sensitizing maximum and range and the relative speed at the sensitizing maximum for each dye was determined from this curve.

The results of the tests are presented in Table 2. Control A in each set is an undyed coating and Control B is a coating containing the known excellent sensitizer 3',9-diethyl-5'-methoxy-5-phenyl-3-(3-sulfobutyl)oxaselenacarbocyanine. The results indicate that good spectral sensitization of radiation-sensitive silver halide compositions can be achieved with the dyes of the invention.

TABLE 2

| Dye | Dye Conc. Moles/Mole AgX × $10^{-4}$ | Relative 400 nm Speed | Sensitizing Maximum (nm) | Relative Speed at Maximum | Sensitizing Range (nm) | Fog |
|---|---|---|---|---|---|---|
| Control A | — | 100 | — | — | 380–500 | .10 |
| Control B | 6.0 | 191 | 610 | 100 | 480–670 | .10 |
| Example 1 | 6.0 | 120 | 550 | 26 | 480–600 | .25 |
| Example 2 | 8.0 | 135 | 520 | 60 | 460–570 | .14 |
| Example 3 | 6.0 | 129 | 560 | 50 | 460–620 | .12 |
| Example 4 | 6.0 | 110 | 580 | 35 | 480–640 | .14 |
| Example 5 | 8.0 | 89 | 580 | 23.5 | 480–640 | .15 |
| Example 6 | 6.0 | 120 | 540 | 34 | 460–600 | .12 |
| Control A | — | 100 | — | — | 380–500 | .06 |
| Control B | 6.0 | 186 | 610 | 100 | 490–670 | .06 |
| Example 7 | 6.0 | 129 | 590 | 28 | 490–650 | .04 |
| Example 8 | 6.0 | 138 | 580 | 21.5 | 490–630 | .04 |
| Example 9 | 6.0 | 129 | 580 | 21.5 | 490–630 | .07 |
| Example 10 | 2.0 | 170 | 710 | 1.0 | 650–750 | .06 |
| Example 11 | 8.0 | 95 | 510 | 4.5 | 490–550 | .06 |
| Example 12 | 6.0 | 166 | 550 | 85 | 470–610 | .06 |
| Example 13 | 6.0 | 155 | 620 | 31 | 490–670 | .07 |
| Example 14 | 6.0 | 214 | 590 | 25 | 500–640 | .08 |
| Example 15 | 8.0 | 138 | 490 | 57 | 440–540 | .07 |
| Control A | — | 100 | — | — | 380–500 | .06 |
| Control B | 6.0 | 209 | 610 | 100 | 490–670 | .07 |
| Example 16 | 8.0 | 123 | 610 | 11.5 | 500–660 | .07 |
| Example 17 | 2.0 | 209 | — | — | 380–500 | .07 |
| Example 18 | 8.0 | 115 | 520 | 4.5 | 510–570 | .07 |
| Example 19 | 6.0 | 209 | 560 | 46 | 470–620 | .07 |
|  | 8.0 | 214 | 560 | 46 | 470–620 | .07 |
| Example 20 | 6.0 | 219 | 560 | 53 | 460–650 | .07 |
|  | 8.0 | 209 | 560 | 54 | 460–650 | .07 |

The invention has been described in detail with reference to particular preferred embodiments thereof but it will be recognized that variations and modifications can be effected within the spirit and scope of the invention.

What is claimed is:

1. In a radiation-sensitive silver-halide composition the improvement wherein said composition is spectrally sensitized by means of a methine dye comprising first and second nuclei joined by a methine linkage, at least said first nucleus comprising a heterocyclic nitrogen ring or ring system having a trialkylsilylalkyl group attached to a nitrogen atom thereof, said nitrogen atom being in conjugation with said methine linkage.

2. The radiation-sensitive silver-halide composition of claim 1 wherein each of said first and second nuclei of said methine dye comprises a heterocyclic nitrogen ring or ring system and each has a trialkylsilylalkyl group attached to a nitrogen atom thereof, each said nitrogen atom being in conjugation with said methine linkage.

3. A radiation-sensitive silver-halide composition containing a spectral sensiziting amount of a methine dye represented by the structure formula

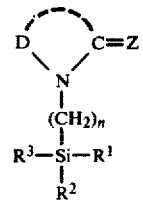

wherein:
D represents atoms which complete a substituted or unsubstituted heterocyclic ring or fused heterocyclic ring system constituting a first nucleus;
Z represents atoms to complete a methine dye, including a methine linkage, a second nucleus, and if necessary, an associated ion to maintain charge neutrality;
$R^1$, $R^2$ and $R^3$ are the same or different alkyl groups having from 1 to 3 carbon atoms; and
n is an integer from 1 to 6.

4. The radiation-sensitive silver-halide composition of claim 3, wherein said methine dye is represented by the structural formula

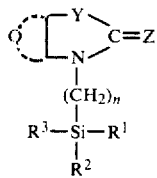

wherein:

Q represents atoms which complete a substituted or unsubstituted fused heterocyclic ring system constituting said first nucleus;

Z represents atoms to complete a methine dye, including said methine linkage, said second nucleus, and, if necessary, an associated ion to maintain charge neutrality;

$R^1$, $R^2$, and $R^3$ are the same or different alkyl groups having from 1 to 3 carbon atoms;

n is an integer from 1 to 6; and

Y represents S, Se, O, or

wherein R represents substituted or unsubstituted alkyl having from 1 to 5 carbon atoms or substituted or unsubstituted aryl.

5. The radiation-sensitive silver-halide composition of claim 1 wherein said first and second nuclei are the same or different and are chosen from the group consisting of a thiazole nucleus, an oxazole nucleus, a selenazole nucleus, a thiazoline nucleus, a quinoline nucleus, an indole nucleus, a pyridine nucleus, an imidazole nucleus, and an imidazole-quinoxaline nucleus.

6. The radiation-sensitive silver-halide composition of claim 1 wherein said second nucleus is selected from the group consisting of a 2-pyrazolin-5-one nucleus, a pyridimine nucleus, a rhodanine nucleus, a hydantoin nucleus, a thiohydantoin nucleus, and an oxazolidinedione nucleus.

7. In a radiation-sensitive silver-halide composition, the improvement wherein said composition is spectrally sensitized by means of a methine dye selected from the group consisting of:

(1) 5,5',6,6'-tetrachloro-1,1-diethyl-3,3'-bis(3-trimethylsilylpropyl)benzimidazolocarbocyanine iodide;

(2) 5,6-dichloro-1,3'-diethyl-3-(3-trimethylsilylpropyl)benzimidazolooxacarbocyanine iodide;

(3) 5,6-dichloro-1,3'-diethyl-3-(3-trimethylsilylpropyl)benzimidazolothicarbocyanine iodide;

(4) 5,6-dichloro-1,3'-diethyl-3-(3-trimethylsilylpropyl)-4',5'-benzobenzimidazolothiocarbocyanine iodide;

(5) 5-{[5,6-dichloro-1-ethyl-3-)3-trimethylsilylpropyl)-2-benzimidazolinylidene]ethylidene}-3-ethylrhodanine;

(6) 5-{[5,6-dichloro-1-ethyl-3-(3-trimethylsilylpropyl)-2-benzimidazolinylidene]ethylidene}-3-ethyl-2-thio-2,4-oxazolidinedione;

(7) 3,3'-Bis(3-trimethylsilylpropyl)thiacarbocyanine iodide;

(8) 9-methyl-3,3'-bis(3-trimethylsilylpropyl)thiacarbocyanine iodide;

(9) 9-ethyl-3,3'-bis(3-trimethylsilylpropyl)thiacarbocyanine iodide;

(10) 3,3'-bis(3-trimethylsilylpropyl)thiadicarbocyanine iodide;

(11) 1'-ethyl-3-(3-trimethylsilylpropyl)thia-2'-cyanine iodide;

(12) 3-ethyl-3'-(3-trimethylsilylpropyl)oxathiacarbocyanine iodide;

(13) 3-ethyl-3'-(3-trimethylsilylpropyl)-4,5-benzothiacarbocyanine iodide;

(14) 5-{[3-(3-trimethylsilylpropyl)-2-benzothiazolinylidene]ethylidene}-3-ethylrhodanine;

(15) 2-(3,3-dicyanoallylidene)-3-(3-trimethylsilylpropyl)benzothiazoline;

(16) 3,3'-bis(3-trimethylsilylpropyl)selenacarbocyanine iodide;

(17) 3,3'-bis(3-trimethylsilylpropyl)selenadicarbocyanine iodide;

(18) 1'-ethyl-3-(3-trimethylsilylpropyl)selena-2'-cyanine iodide;

(19) 3-ethyl-3'-(3-trimethylsilylpropyl)oxaselenocarbocyanine iodide; and

(20) 5,6-dichloro-1,3-diethyl-3'-(3-trimethylsilylpropyl)benzimidazoloselenacarbocyanine iodide.

8. A radiation-sensitive silver-halide photographic element comprising a support having thereon at least one layer comprising the radiation-sensitive silver halide composition of claims 1, 2, 3, 4, 5, 6, or 7.

9. A radiation-sensitive composition comprising silver halide and a spectrally sensitizing quantity of a methine dye comprising first and second nuclei joined by a methine linkage, at least said first nucleus comprising a heterocyclic nitrogen ring or ring system having a trialkylsilylalkyl group attached to a nitrogen atom thereof, said nitrogen atom being in conjugation with said methine linkage.

* * * * *